Sept. 23, 1969 R. S. MOORE Plant Pat. 2,921
MINIATURE ROSE PLANT
Filed Feb. 19, 1968
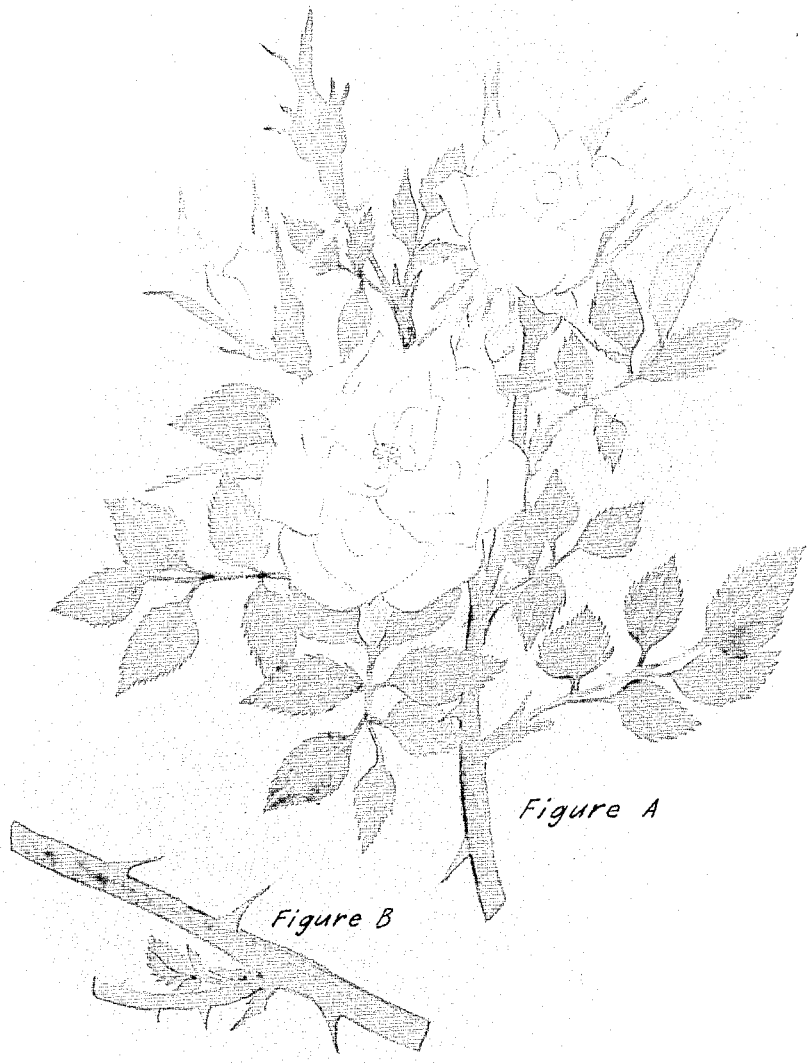
WITNESS
Jeanette Nunn Copley
INVENTOR
RALPH S. MOORE

United States Patent Office

Plant Pat. 2,921
Patented Sept. 23, 1969

2,921
MINIATURE ROSE PLANT

Ralph S. Moore, 2519 E. Noble Ave.,
Visalia, Calif. 93277

Filed Feb. 19, 1968, Ser. No. 706,725
Int. Cl. A01h 5/02
U.S. Cl. Plt.—8 1 Claim The present invention relates to a new and distinct variety of hardy, dwarf, bush type rose plant of the miniature class; the variety being primarily characterized—as to novelty—by yellow buds and flowers which in general color effect are bright lemon yellow.

The variety is further characterized by:

An abundance of bloom, with flowers borne singly or several to stem.

Moderate fragrance.

A plant which is vigorous, of rounded upright shape, and with glossy, small foliage with pointed leaflets; the flowers and foliage being similar to the variety Yellow Doll (United States Plant Patent No. 2,450), but more compact and dwarf in plant habit with buds and flowers a more intense and lasting yellow color. The plant which has a normal average height of about 12″ at maturity can be easily maintained at 10″ or less by occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, Calif., under conditions of careful control and observation, as a cross between Golden Glow, a climber (United States Plant Patent No. 263, expired), as the seed parent and Magic Wand (not patented) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color identification are employed.

Type: Hardy; dwarf; bush; seedling; greenhouse; outdoors; garden decoration; potted plant.

Class: Miniature.

Flowers:

*Continuity.*—Continuous; repeat blooms all season.

*Fragrance.*—Slight or moderate.

Flowers borne: Singly and several together on short, thin but sturdy, wire-like stem.

Quantity of bloom: Abundance, average or above both outside and inside greenhouse.

Bud: Peduncle—short, about ¾″ to 1″; slender but sturdy; erect; medium green; smooth except for a few tiny soft hairs. Before calyx breaks: size—small. Form—long; pointed, usually with several small leafy appendages on surface of bud; with foliaceous parts extending beyond the tip of the bud equal to ½ or more of its length. Color—medium green. As calyx breaks—color yellow (sometimes greenish-yellow). As first petal opens: lemon yellow; size—small. Color—outside: Lemon Yellow 4/1 tinted with pale green at base; inside: Aureolin Yellow 3/1 shading into Aureolin Yellow 3 on lower half of petal. Form—medium long; pointed. Opening—usually opens well in all weather.

Bloom: Size when fully open—small, averaging 1¼″ or slightly larger. Petalage—double—about 40 petals; sometimes with several narrow petaloids. Form—high centered, moderately full at first; with petals rolled loosely outward, and later at maturity petals almost flat with stamens showing.

Petals: Fairly thick; satiny both inside and outside. Shape—outside petals broad lanceolate with nearly round tip; intermediate—medium to broad lanceolate, nearly round tip; inside—lanceolate, rounded tip.

Color: Newly opened flower from a plant in greenhouse (December 1967), Visalia, Calif. Opening bud and flower color tends to be more Lemon Yellow indoors during short days (winter) and may be more Cobalt Yellow (Aureolin Yellow 3/1) during normal (spring, summer and fall) growing season (both indoors and outdoors).

*Outside petal.*—Outside surface—Lemon Yellow 4/1, deeper yellow at base. Inside surface—Aureolin Yellow 3/1 shading deeper yellow at base.

*Intermediate petal.*—Outside surface—Lemon Yellow 4/2, deeper yellow at base. Inside surface—Aureolin Yellow 3/1, shading deeper at base.

*Inside petal.*—Same as intermediate petal.

*General color effects.*—Newly opened flower—bright clear yellow. Three days open—Lemon yellow.

*Behaviour.*—Petals drop clean.

*Flower longevity* (May-June—bush in garden 5 days or longer).—Cut flowers kept at living room temperature—up to 7 days.

Reproductive organs:

*Stamens.*—Moderate amount; yellow; sometimes mixed with petaloids.

*Anthers.*—Moderate amount; golden.

*Pollen.*—Sparse; usually none.

*Pistils.*—Moderate number.

*Styles.*—Even; short; very slender; pale yellow.

*Stigma.*—Often not well formed; same color as style.

*Ovaries.*—All enclosed in calyx.

*Hips.*—None.

*Sepals.*—Spear shaped; recurved; usually drop off with peduncle.

*Seeds.*—None.

Foliage:

*Leaves.*—Compound of 5 (occasionally 3 or 7) leaflets—abundant, small, leathery, glossy.

*Leaflets.*—Shape—lanceolate; apex acute; base rounded. Margin—serrate. Color—medium green; new growth green. Rachis—medium strength; upper surface grooved with a few very tiny short hairs; under side sparsely thorny. Stipules—medium to long (for a miniature); narrow, medium length points, turning out at an angle of about 45 degrees.

Growth:

*Habit.*—Dwarf, bushy; moderately spreading; much branched.

*Growth.*—Free; vigorous (very compact).

*Canes.*—Slender; medium.

*Main stems.*—Color—medium green. Thorns—moderately thorny; small oval base; medium length; hooked slightly downward. Color—gray-brown. Prickles—none. Hairs—none.

*Branches.*—Color—medium green. Thorns—moderately thorny; medium length; hooked slightly downward. Color—brownish.

*New shoots.*—Color—medium green, sometimes lightly tinted reddish. Thorns—moderately thorny; medium length; hooked very slightly downward;

short oval base. Color—reddish. Prickles—none. Hairs—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, as illustrated and described, characterized by buds and flowers resembling the Yellow Doll (Plant Patent No. 2,450) miniature rose in general effect but showing fewer and generally broader petals in the open flower, brighter yellow color of both buds and flowers with less tendency to fade, the buds generally smaller and held more erect than Yellow Doll; and further characterized by a plant which is vigorous and yet more compact in growth than Yellow Doll, easy to propagate from cuttings, with small medium green glossy foliage and an abundance of bloom, with flowers borne singly or several to the stem in loose clusters.

No references cited.

ROBERT E. BAGWILL, Primary Examiner